(12) United States Patent
Ott et al.

(10) Patent No.: US 7,641,911 B2
(45) Date of Patent: *Jan. 5, 2010

(54) IMMUNOLOGICAL ADJUVANT COMPOSITIONS

(75) Inventors: Gary S. Ott, Oakland, CA (US); Manmohan Singh, Hercules, CA (US); Derek O'Hagan, Berkeley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 653 days.

This patent is subject to a terminal disclaimer.

(21) Appl. No.: 11/042,745

(22) Filed: Jan. 25, 2005

(65) Prior Publication Data

US 2005/0123599 A1    Jun. 9, 2005

Related U.S. Application Data

(63) Continuation of application No. 10/103,673, filed on Mar. 21, 2002, now Pat. No. 6,861,410.

(51) Int. Cl.
*A61K 39/29* (2006.01)

(52) U.S. Cl. ............... 424/283.1; 424/184.1; 424/278.1

(58) Field of Classification Search ........................ None
See application file for complete search history.

(56) References Cited

U.S. PATENT DOCUMENTS

| 4,806,350 | A | * | 2/1989 | Gerber ..................... 424/198.1 |
| 4,900,549 | A | | 2/1990 | De Vries et al. |
| 5,118,671 | A | | 6/1992 | Bombardelli et al. |
| 5,688,772 | A | | 11/1997 | Estrada et al. |
| 5,880,103 | A | | 3/1999 | Urban et al. |
| 5,914,113 | A | | 6/1999 | Schrier |
| 5,976,604 | A | | 11/1999 | Kunieda et al. ............. 426/602 |
| 6,080,725 | A | * | 6/2000 | Marciani ..................... 514/26 |
| 6,086,901 | A | | 7/2000 | O'Hagan et al. |
| 6,299,884 | B1 | | 10/2001 | Van Nest et al. |
| 6,306,405 | B1 | | 10/2001 | O'Hagan et al. |
| 6,342,224 | B1 | | 1/2002 | Bruck et al. |
| 6,372,227 | B1 | * | 4/2002 | Garcon et al. ............. 424/283.1 |
| 6,861,410 | B1 | * | 3/2005 | Ott et al. ..................... 514/26 |

FOREIGN PATENT DOCUMENTS

| EP | 0 822 831 B1 | 1/1996 |
| WO | WO 90/03184 | 4/1990 |
| WO | WO 98/57659 | 12/1998 |
| WO | WO 99/12565 | 3/1999 |
| WO | WO 00/43511 | 7/2000 |

OTHER PUBLICATIONS

Bomford et al., "Adjuvanticity and ISCOM Formation by Structurally Diverse Saponins", 1992, Vaccine, 10(9):572-577.
Guy et al., "Design, Characterization and Preclinical Efficacy of a Cationic Lipid Adjuvant for Influenza Split Vaccine", 2001, Vaccine, 19:1794-1805.
Sanchez et al., "Formulations of Single of Multiple H. Pylori Antigens with DC Chol Adjuvant Induce Protection by the Systemic Route in Mice Optimal Prophylactic Combinations are Different from Therapeutic Ones", 2001, FEMS Immunology and Medical Microbiology, 30:157-165.
Singh et al., "Advances in Vaccine Adjuvants", 1999, Nature Biotechnology, 17(11):1075-1081.
Sjolander et al., "Uptake and Adjuvant Activity of Orally Delivered Saponin and ISCOM™ Vaccines" 1998, Adv. Drug Delivery Rev., 34:321-338.
Mowat et al., "ISCOMS—A Novel Strategy for Mucosal Immunization?" 1991, 'Immunology Today, 12:383-385.
Takahashi et al., "Induction of CD8 Cytotoxic T Cells by Immunization with Purified HIV-1 Envelope Protein in ISCOMs", 1990, Nature, 344:873-875.

* cited by examiner

*Primary Examiner*—Traviss C McIntosh, III
(74) *Attorney, Agent, or Firm*—Helen Lee; Robert Gorman; David Bonham

(57) ABSTRACT

The present invention is directed to novel adjuvant compositions, which target the cellular and/or humoral arms of immunity. According to an embodiment of the invention, an oil-in-water adjuvant composition is provided that comprises: (a) water; (b) a metabolizable oil comprising at least one branched or unbranched long-chain hydrocarbon moiety; (c) a steroid; and (d) a saponin.

29 Claims, 2 Drawing Sheets

IMMUNOLOGICAL ADJUVANT COMPOSITIONS

STATEMENT OF RELATED APPLICATIONS

This application is a continuation of U.S. patent application Ser. No. 10/103,673, filed Mar. 21, 2002 now U.S. Pat. No. 6,861,410 and entitled "Immunological Adjuvant Compositions," which is incorporated by reference in its entirety herein.

INTRODUCTION

1. Technical Field

The present invention relates generally to pharmaceutical compositions. More particularly, the present invention relates to immunological adjuvants comprising oil-in-water emulsions.

2. Background

Traditional live anti-viral vaccines typically require no immunological adjuvants. Similarly, killed virus vaccines are generally much more immunogenic than attenuated pathogen or subunit protein vaccines and, like live anti-viral vaccines, can be effective with no adjuvant or with adjuvants that have limited ability to stimulate immune responses. Recently developed attenuated pathogen or subunit protein vaccines, while offering significant advantages over the traditional vaccines in terms of safety and cost of production, generally have limited immunogenicity compared to whole viruses. As a result, these vaccines typically require adjuvants with significant immunostimulatory capability to reach their full potential in preventing disease.

A number of immunological adjuvants are known in the art, several of which will be briefly mentioned here.

Aluminum salts (alum) have been useful for some vaccines including hepatitis B, diphtheria, polio, rabies and influenza, but may not be useful for others, especially if stimulation of cell-mediated immunity is required for protection. Reports indicate that alum failed to improve the effectiveness of whooping cough and typhoid vaccines and provided only a slight effect with adenovirus vaccines. Problems with alum include induction of granulomas at the injection site and lot-to-lot variation of alum preparations.

Complete Freund's adjuvant (CFA) is a powerful immunostimulatory agent that has been successfully used with many antigens on an experimental basis. CFA includes three components: a mineral oil, an emulsifying agent, and killed mycobacteria, such as Mycobacterium tuberculosis. Aqueous antigen solutions are mixed with these components to create a water-in-oil emulsion. Although effective as an adjuvant, CFA causes severe side effects primarily due to the presence of the mycobacterial component, including pain, abscess formation and fever. CFA, therefore, is not used in human and veterinary vaccines.

Incomplete Freund's adjuvant (IFA) is similar to CFA but does not include the bacterial component. IFA, while not approved for use in the United States, has been used elsewhere in human vaccines for influenza and polio and in veterinary vaccines for rabies, canine distemper and foot-and-mouth disease. However, evidence indicates that both the oil and emulsifier used in IFA can cause tumors in mice.

Muramyl dipeptide (MDP) has been found to be the minimal unit of the mycobacterial cell wall complex that generates the adjuvant activity observed with CFA. See, e.g., Ellouz et al., Biochem. Biophys. Res. Commun. (1974) 59:1317. Several synthetic analogs of MDP have been generated that exhibit a wide range of adjuvant potency and side effects. For a review of these analogs, see, Chedid et al., Prog. Allergy (1978) 25:63. Representative analogs of MDP include threonyl derivatives of MDP (Byars et al., Vaccine (1987) 5:223), n-butyl derivatives of MDP (Chedid et al., Infect. Immun. 35:417), and a lipophilic derivative of a muramyl tripeptide (Gisler et al., in Immunomodulations of Microbial Products and Related Synthetic Compounds (1981) Y. Yamamura and S. Kotani, eds., Excerpta Medica, Amsterdam, p. 167). One lipophilic derivative of MDP is N-acetylmuramyl-L-alanyl-D-isogluatminyl-L-alanine-2-(1'-2'-dipalmitoyl-sn-glycero-3-huydroxyphosphoryloxy)-ethylamine (MTP-PE). This muramyl tripeptide includes phospholipid tails that allow association of the hydrophobic portion of the molecule with a lipid environment while the muramyl peptide portion associates with the aqueous environment. Thus, the MTP-PE itself is able to act as an emulsifying agent to generate stable oil-in-water emulsions. MTP-PE has been used in an emulsion of 4% squalene with 0.008% TWEEN 80®, termed MTP-PE-LO (low oil), to deliver the herpes simplex virus gD antigen with effective results (Sanchez-Pescador et al., J. Immunol. (1988) 141:1720-1727), albeit poor physical stability.

Recently, MF59, a safe, highly immunogenic, submicron oil-in-water emulsion which contains 4-5% w/v squalene, 0.5% w/v Tween® 80, 0.5% Span® 85, and optionally, varying amounts of MTP-PE, has been developed for use in vaccine compositions. See, e.g., Ott et al., "MF59—Design and Evaluation of a Safe and Potent Adjuvant for Human Vaccines" in Vaccine Design: The Subunit and Adjuvant Approach (Powell, M. F. and Newman, M. J. eds.) Plenum Press, New York, 1995, pp. 277-296.

QS21, a saponin extracted from the bark of the South American soap bark tree *Quillaja saponaria* Molina, is another adjuvant that has been shown to have significant immunological activity (Kensil, et al., 1991; Wu, et al., 1992; White, et al., 1991). See, e.g., White, A. C., Cloutier, P. and Coughlin, R. T. A purified saponin acts as an adjuvant for a T-independent antigen. Adv. Exp. Med. Biol. 303:207-210, 1991; Wu, J. Y., Gardner, B. H., Murphy, C. I., Seals, J. R., Kensil, C. R., Recchia, J., Beltz, G. A., Newman, G. W. and Newman, M. J. Saponin adjuvant enhancement of antigen-specific immune responses to an experimental HIV-1 vaccine. J. Immunol. 148:1519-1525, 1992; Kensil, C. R., Patel, U., Lennick, M. and Marciani, D. Separation and characterization of saponins with adjuvant activity from Quillaja saponaria Molina cortex. J. Immunol. 146:431-437, 1991.

Immunostimulating complexes (ISCOMs) containing a saponin, a sterol and, optionally, a phospholipid are also known. For example, U.S. Pat. No. 4,900,549 teaches a process for preparing immunogenic complexes containing an amphiphatic antigenic protein or peptide, a sterol, and a glycoside comprising hydrophobic and hydrophilic regions. Optionally, the complexes also contain a phospholipid, preferably phosphatidylethanolamine. The preferred sterol is cholesterol, and preferred glycosides are saponins, especially Quil A (a *Quillaja saponaria* Molina saponin extract). Methods for producing ISCOMs are known in the art and described in e.g., U.S. Pat. Nos. 5,118,671, 4,900,549, International Publication No. WO 90/03184 and Bomford et al. Vaccine (1992) 10:572-577. Protective immunity has been generated in a variety of experimental models of infection, including toxoplasmosis and Epstein-Barr virus-induced tumors, using ISCOMs as the delivery vehicle for antigens (Mowat and Donachie, Immunology Today 12:383-385, 1991). Doses of antigen as low as 1 ug encapsulated in ISCOMS have been found to produce class I mediated CTL responses, where either purified intact HIV-1-IIIB gp160 envelope glycoprotein or influenza hemagglutinin is the antigen (Takahashi et al., Nature 344:873-875, 1990).

SUMMARY OF THE INVENTION

The present invention is directed to novel adjuvant compositions, which target the cellular and/or humoral arms of immunity.

According to one aspect of the present invention, an oil-in-water adjuvant composition is provided, which comprises: (a) water; (b) a metabolizable oil comprising at least one branched or unbranched long-chain hydrocarbon moiety; (c) a steroid; (d) a saponin, (e) optionally, at least one emulsifying agent (in addition to the saponin) and (f) optionally, a muramyl tripeptide.

Typically, the metabolizable oil is selected from an animal oils (including fish oils) and a vegetable oils. Examples of metabolizable oils include fatty acids having from 10-30 carbon atoms, as well as mono-, di- and tri-glycerides having fatty acid moieties of 10-30 carbon atoms. Preferred metabolizable oils are unsaturated hydrocarbons having from 20-40 carbons, more preferably, branched, polyunsaturated hydrocarbon having from 20-40 carbon atoms, including terpenoids such as squalene.

The steroid is preferably a sterol, more preferably cholesterol.

Preferred saponins are triterpenoidal saponins and include saponins extracted from *Quillaja saponaria*.

The optional at least one emulsifying agent preferably comprises at least one non-ionic detergent. Preferred emulsifying agents include fatty acid esters as well as fatty acid esters comprising a polyoxyethylene moiety. Preferred emulsifying agents also include sorbitan derivatives, such as sorbitan fatty acid monoesters, sorbitan fatty acid sesquiesters, sorbitan fatty acid triesters, polyoxyethylene sorbitan fatty acid monoesters and polyoxyethylene sorbitan fatty acid triesters. The combination of polyoxyethylene sorbitan monooleate and sorbitan trioleate is particularly preferred.

In preferred embodiments, the oil-in-water adjuvant composition further comprises an antigen, such as a polypeptide antigen or polynucleotide antigen. Preferred antigens include HIV polypeptide antigens, meningitis B polypeptide antigens, streptococcus B polypeptide antigens and Influenza A hemagglutinin polypeptide antigens, as well as nucleotides encoding the same.

The oil-in-water adjuvant compositions of the invention can be administered to a vertebrate subject to deliver a therapeutically effective amount of an antigen to the subject.

According to another aspect of the present invention, a method of producing an oil-in-water adjuvant composition is provided. The method comprises: (a) forming an emulsion comprising (i) water, (ii) a water-immiscible organic solvent, (iii) a metabolizable oil comprising at least one branched or unbranched long-chain hydrocarbon moiety, (iv) a steroid, and (v) a saponin; and (b) removing the organic solvent from the emulsion.

In some preferred embodiments, the emulsion in step "(a)" immediately above is an oil-in-water emulsion that is formed by a process comprising: (i) providing a water-based phase comprising the water and the saponin, (ii) providing a solvent-based phase comprising the water-immiscible solvent, the steroid and the metabolizable oil, and (iii) emulsifying the water-based phase with the solvent-based phase to form the oil-in-water emulsion.

In other preferred embodiments, the emulsion of step "(a)" further comprises at least one emulsifying agent. In a specific preferred embodiment, where the at least one emulsifying agent includes polyoxyethylene sorbitan monooleate and sorbitan trioleate, the emulsion is preferably an oil-in-water emulsion formed by a process that comprises: (a) providing a water-based phase comprising the water, the saponin and the polyoxyethylene sorbitan monooleate; (b) providing a solvent-based phase comprising the water-immiscible solvent, the steroid, the metabolizable oil and the sorbitan trioleate; and (c) emulsifying the water-based phase with the solvent-based phase to form an oil-in-water emulsion.

One advantage of the present invention is that a novel adjuvant composition is provided that can be used for the treatment of disease.

Another advantage of the present invention is that a novel adjuvant composition is provided that can be used for a vaccine.

Yet another advantage of the present invention is that a novel adjuvant composition is provided that can be used for raising an immune response, including enhanced cellular and/or humoral immunity.

These and other embodiments and advantages of the present invention will readily occur to those of ordinary skill in the art in view of the disclosure herein.

DETAILED DESCRIPTION OF THE INVENTION

Figure 1:
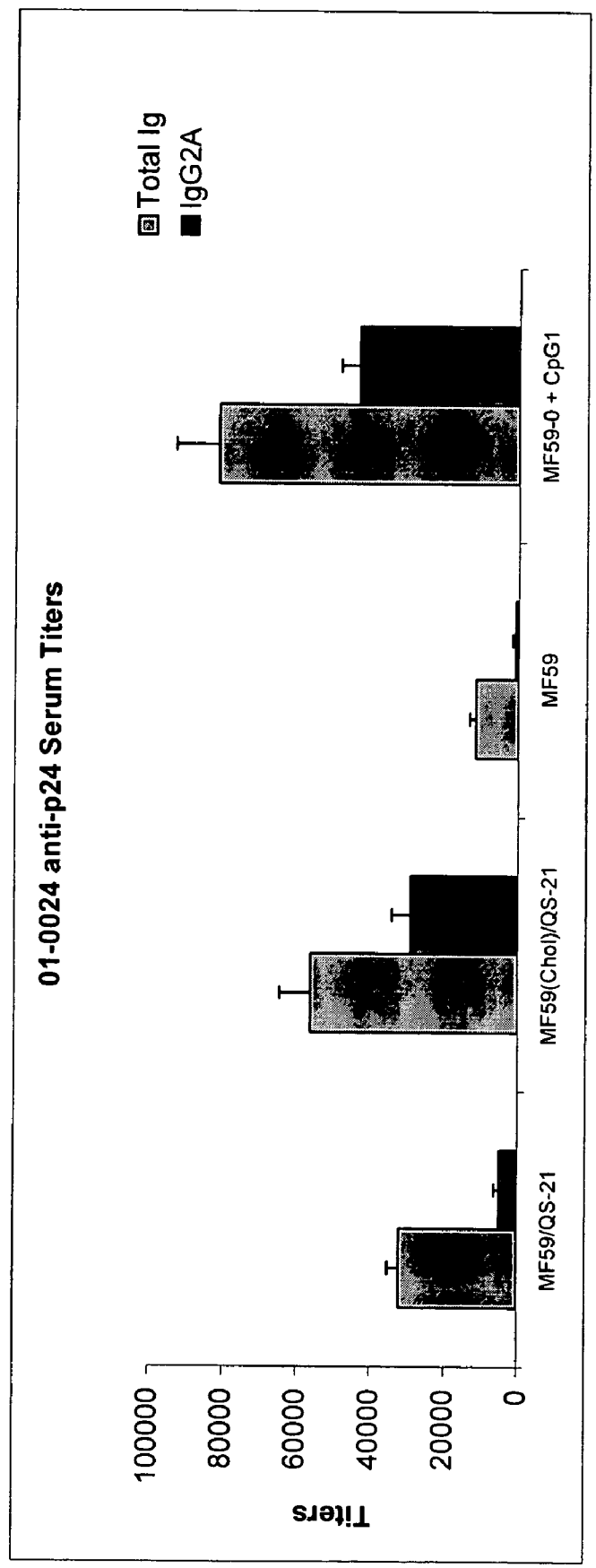
FIG. 1 is a bar graph illustrating IgG and IgG2a serum titers for four injectable formulations.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); *Handbook of Experimental Immunology,* Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher=s Polymer Chemistry* (4th edition, Marcel Dekker Inc., 1996).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Unless stated otherwise, all percentages and ratios herein are given on a weight basis.

Definitions

In describing the present invention, the following terms will be employed, and are intended to be defined as indicated below.

The term "pharmaceutical" refers to biologically active compounds such as antibiotics, antiviral agents, growth factors, hormones, and the like, discussed in more detail below.

The term "adjuvant" refers to any substance that assists or modifies the immunological action of a pharmaceutical composition, including but not limited to adjuvants that increase or diversify the immune response to an antigen.

"Oil" as defined herein, is a liquid that is immiscible with water.

"Steroids" as defined herein are derivatives of perhydrocyclopentanophenanthrene, a saturated tetracyclic hydrocarbon, and include sterols, bile acids and hormones such as adrenal cortical steroids, androgens, estrogens and pregestational hormones.

"Saponins" as defined herein are glycoside compounds that produce foaming solutions. They are found in many plants, and they get their name from the soapwort plant (*Saponaria*), the root of which was used historically as a soap. Saponins are sometimes referred to as "natural detergents" due to their distinctive foaming characteristics.

A "polynucleotide" is a nucleic acid polymer, which typically encodes a biologically active (e.g., immunogenic) protein or polypeptide. Depending on the nature of the polypeptide encoded by the polynucleotide, a polynucleotide can include as little as 10 nucleotides, e.g., where the polynucleotide encodes an antigen. Furthermore, a "polynucleotide" can include both double- and single-stranded sequences and refers to, but is not limited to, cDNA from viral, prokaryotic or eukaryotic mRNA, genomic RNA and DNA sequences from viral (e.g. RNA and DNA viruses and retroviruses) or prokaryotic DNA, and especially synthetic DNA sequences. The term also captures sequences that include any of the known base analogs of DNA and RNA. The term further includes modifications, such as deletions, additions and substitutions (generally conservative in nature), to a native sequence, preferably such that the nucleic acid molecule encodes, for example, an antigenic protein. These modifications may be deliberate, as through site-directed mutagenesis, or may be accidental, such as through mutations of hosts which produce the antigens.

As used herein, the phrase "nucleic acid" refers to DNA, RNA, as well as any of the known base analogs of DNA and RNA or chimeras formed therefrom.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, preferably such that the protein maintains the ability to elicit an immunological response within a subject to which the protein is administered.

By "antigen" is meant a molecule that contains one or more epitopes capable of stimulating a host's immune system to make a cellular antigen-specific immune response or a humoral antibody response when the antigen is presented in accordance with the present invention. Normally, an epitope will include between about 3-15, generally about 5-15, amino acids. Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an immunogenic protein, or antigenic determinant in vivo, such as in nucleic acid immunization applications, is also included in the definition of antigen herein.

Further, for purposes of the present invention, antigens can be derived from any of several known viruses, bacteria, parasites and fungi, as well as any of the various tumor antigens. Furthermore, for purposes of the present invention, an "antigen" refers to a protein that includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts that produce the antigens.

An "immunological response" to an antigen or composition is the development in a subject of a humoral and/or a cellular immune response to molecules present in the antigen or composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition or vaccine that elicits a cellular immune response, may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., *J. Immunol.* (1993) 151:4189-4199; Doe et al., *Eur. J. Immunol.* (1994) 24:2369-2376.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A adjuvant composition which contains a selected antigen, displays "enhanced immunogenicity" when it possesses a greater capacity to elicit an immune response than the immune response elicited by an equivalent amount of the antigen when delivered without association with the adjuvant. Such enhanced immunogenicity can be determined, for example, by administering the adjuvant/antigen composition, and antigen controls to animals and performing an appropriate immunoassay (or immunoassays).

The terms "effective amount" and "pharmaceutically effective amount" of the adjuvant/antigen composition, as provided herein, refer to a sufficient amount of the adjuvant/antigen composition to treat a condition of interest. For example, these expressions may refer to an amount sufficient to provide a desired response, such as an immunological response, and corresponding therapeutic effect. As will be pointed out below, the exact amount required will vary from subject to subject, depending on the species, age, and general condition of the subject, the severity of the condition being treated, the particular antigen of interest, the mode of administration, and the like. An appropriate "effective" amount in any individual case may be determined by one of ordinary skill in the art using routine experimentation.

The term "excipient" refers to substances that are commonly provided within finished dosage forms, and include vehicles (water, saline, buffer solutions, glycerol, polyethylene glycol, hyaluronic acid, ethanol, etc.), binders, disintegrants, fillers (diluents), lubricants, glidants (flow enhancers), compression aids, colors, sweeteners, preservatives, suspensing/dispersing agents, film formers/coatings, flavors and printing inks.

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

By "pharmaceutically acceptable" or "pharmacologically acceptable" is meant a material which is not biologically or otherwise undesirable, i.e., the material may be administered to an individual without causing any undesirable biological effects in the individual or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" (including variations thereof, for example, "treat" or "treated") refers to any of (i) the prevention of infection or reinfection, as in a traditional vaccine, (ii) the reduction or elimination of symptoms, and (iii) the substantial or complete elimination of the pathogen or disorder in question. Hence, treatment may be effected prophylactically (prior to infection) or therapeutically (following infection).

According to some embodiments of the present invention, compositions and methods are provided which treat, including prophylactically and/or therapeutically immunize, a host animal against viral, fungal, mycoplasma, bacterial, or protozoan infections, as well as to tumors. The methods of the present invention are useful for conferring prophylactic and/or therapeutic immunity to a mammal, preferably a human. The methods of the present invention can also be practiced on mammals, other than humans, including biomedical research applications.

General Methods

The adjuvant compositions of present invention can be used to enhance the immunogenicity of a wide variety of antigens including, but not limited to, antigenic polypeptides and polynucleotides that encode antigenic polypeptides.

A particular advantage of the adjuvant/antigen compositions of the present invention is their ability to generate both humoral and cell-mediated immune responses in a vertebrate subject. The ability of the antigen/adjuvant compositions of the present invention to elicit a cell-mediated immune response against a selected antigen provides a powerful tool against infection by a wide variety of pathogens. Accordingly, the antigen/adjuvant compositions of the present invention can be incorporated into vaccine compositions.

Thus, in addition to a conventional antibody response, the system herein described can provide for, e.g., the association of antigens with class I MHC molecules such that an in vivo cellular immune response to the antigen of interest can be mounted which stimulates the production of CTLs to allow for future recognition of the antigen. Furthermore, the methods may elicit an antigen-specific response by helper T-cells. Accordingly, the methods of the present invention will find use with any antigen for which cellular and/or humoral immune responses are desired, preferably antigens derived from viral pathogens that may induce antibodies, T-cell helper epitopes and T-cell cytotoxic epitopes. Such antigens include, but are not limited to, those proteins encoded by human and animal viruses and can correspond to either structural or non-structural proteins.

The adjuvant/antigen compositions of the present invention are particularly useful for immunization against intracellular viruses that normally elicit poor immune responses. For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., Cytomegaloviruses (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present composition and methods.

Similarly, the sequence for the 6-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., AHBV Vaccines—from the laboratory to license: a case study@ in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses will also find use in the claimed compositions and methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 or gp140 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids,* 1990, Los Alamos, N. Mex.: Los Alamos National Laboratory; and Modrow et al., *J. Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol and tat regions.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the compositions and methods described herein.

The compositions and methods described herein will also find use with numerous bacterial antigens, such as those derived from organisms that cause diphtheria, cholera, tuberculosis, tetanus, pertussis, meningitis, and other pathogenic states, including, without limitation, *Bordetella pertussis, Neisseria meningitides* (A, B, C, Y), *Neisseria gonorrhoeae, Helicobacter pylori,* and *Haemophilus influenza. Hemophilus influenza* type B (HIB), *Helicobacter pylori*, and combinations thereof. Examples of antigens from *Neisseria meningitides* B are disclosed in the following co-owned patent applications: PCT/US99/09346; PCT IB98/01665; and PCT IB99/00103. Examples of parasitic antigens include those derived from organisms causing malaria and Lyme disease.

Additional antigens for use with the invention, which are not necessarily exclusive of those listed elsewhere in this application, include the following (references are listed below):

A protein antigen from *N. meningitidis* serogroup B, such as those in Refs. 1 to 7 below.

an outer-membrane vesicle (OMV) preparation from *N. meningitidis* serogroup B, such as those disclosed in Refs. 8, 9, 10, 11 etc. below.

a saccharide antigen from *N. meningitidis* serogroup A, C, W135 and/or Y, such as the oligosaccharide disclosed in Ref. 12 below from serogroup C (see also Ref. 13).

a saccharide antigen from *Streptococcus pneumoniae* (e.g. Refs. 14, 15, 16).

an antigen from *N. gonorrhoeae* (e.g., Refs. 1, 2, 3).

an antigen from *Chlamydia pneumoniae* (e.g., Refs. 17, 18, 19, 20, 21, 22, 23).

an antigen from *Chlamydia trachomatis* (e.g. Ref. 24).

an antigen from hepatitis A virus, such as inactivated virus (e.g., Refs. 25, 26).

an antigen from hepatitis B virus, such as the surface and/or core antigens (e.g., Refs. 26, 27).

an antigen from hepatitis C virus (e.g. Ref. 28).

an antigen from *Bordetella pertussis*, such as pertussis holotoxin (PT) and filamentous haemaglutinin (FHA) from *B. pertussis*, optionally also in combination with pertactin and/or agglutinogens 2 and 3 (e.g., Refs. 29 & 30).

a diphtheria antigen, such as diphtheria toxoid (e.g., chapter 3 of Ref. 31) e.g. the $CRM_{197}$ mutant (e.g., Ref. 32).

a tetanus antigen, such as a tetanus toxoid (e.g., chapter 4 of Ref. 31).

a protein antigen from *Helicobacter pylori* such as CagA (e.g. Ref. 33), VacA (e.g. Ref. 33), NAP (e.g. Ref. 34), HopX (e.g. Ref. 35), HopY (e.g. Ref. 35) and/or urease.

a saccharide antigen from *Haemophilus influenzae* B (e.g. Ref. 13).

an antigen from *Porphyramonas gingivalis* (e.g. Ref. 36).

polio antigen(s) (e.g. Refs. 37, 38) such as IPV or OPV.

rabies antigen(s) (e.g. Ref. 39) such as lyophilized inactivated virus (e.g. Ref. 40, Rabavert™).

measles, mumps and/or rubella antigens (e.g., chapters 9, 10 and 11 of Ref. 31).

influenza antigen(s) (e.g. chapter 19 of Ref. 31), such as the haemagglutinin and/or neuraminidase surface proteins.

an antigen from *Moraxella catarrhalis* (e.g., time 41).

an antigen from *Streptococcus agalactiae* (Group B streptococcus) (e.g. Refs. 42, 43)

an antigen from *Streptococcus pyogenes* (Group A streptococcus) (e.g. Refs. 43, 44, 45).

an antigen from *Staphylococcus aureus* (e.g. Ref. 46).

Compositions comprising one or more of these antigens.

Where a saccharide or carbohydrate antigen is used, it is preferably conjugated to a carrier protein in order to enhance immunogenicity (e.g. Refs. 47 to 56). Preferred carrier proteins are bacterial toxins or toxoids, such as diphtheria or tetanus toxoids. The $CRM_{197}$ diphtheria toxoid is particularly preferred. Other suitable carrier proteins include *N. meningitidis* outer membrane protein (e.g. Ref. 57), synthetic peptides (e.g. Refs. 58, 59), heat shock proteins (e.g. Ref. 60), pertussis proteins (e.g. Refs. 61, 62), protein D from *H. Influenzae* (e.g. Ref. 63), toxin A or B from *C. difficile* (e.g. Ref. 64), etc. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Saccharides from different serogroups of *N. meningitidis* may be conjugated to the same or different carrier proteins.

Any suitable conjugation reaction can be used, with any suitable linker where necessary.

Toxic protein antigens may be detoxified where necessary (e.g. detoxification of pertussis toxin by chemical and/or means (Ref. 30)).

Where diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

It is readily apparent that the subject invention can be used to deliver a wide variety of antigens and hence to prophylactically or therapeutically treat a large number of diseases. In some embodiments, the antigen/adjuvant compositions of the present invention can be used for site-specific targeted delivery. For example, intravenous administration of the antigen/adjuvant compositions can be used for targeting the lung, liver, spleen, blood circulation, or bone marrow.

Turning now to the adjuvant compositions of the present invention, these compositions are preferably oil-in-water compositions comprising: (a) water; (b) a metabolizable oil comprising at least one branched or unbranched long-chain hydrocarbon moiety; (c) a steroid; (d) a saponin; (e) optionally, at least one emulsifying agent (in addition to the saponin); and (f) also optionally, a muramyl peptide.

The water component of these adjuvant compositions can be essentially any pharmaceutically acceptable water-containing liquid, including deionized water, normal saline, a buffered solution such as buffered saline and the like.

In cases where these compositions are intended for parenteral administration, it is preferable to make up final buffered solutions used as vaccines so that the tonicity, i.e., osmolality, is essentially the same as normal physiological fluids in order to prevent post-administration swelling or rapid absorption of the composition because of differential ion concentrations between the composition and physiological fluids.

It is also preferable to buffer the saline in order to maintain a pH compatible with normal physiological conditions. Also, in certain instances, it may be necessary to maintain the pH at a particular level in order to insure the stability of certain composition components such as glycopeptides. Any physiologically acceptable solution buffer may be used herein, but phosphate buffered solutions are preferred, particularly phosphate buffered saline (PBS). Other acceptable buffers such as acetate, Tris buffered saline, Hank's buffered saline, bicarbonate, carbonate, sodium citrate/ethylenediaminetetraacetic acid, or the like may be used as substitutes for phosphate buffers. The pH of the aqueous component will preferably be between 6.0-8.0.

However, when the adjuvant is initially prepared, unadulterated water may be preferred as the aqueous component of the emulsion, as increasing the salt concentration can make it difficult to achieve the desired small droplet size. When the final vaccine formulation is prepared from the adjuvant, the antigenic material can be added in a buffer at an appropriate osmolality to provide the desired vaccine composition.

The oil component of the adjuvant compositions of the present invention is a metabolizable, non-toxic oil, preferably including, but not limited to, alkanes, alkenes, alkynes, and their corresponding acids and alcohols, as well as the ethers and esters thereof, and mixtures thereof. The oil may be any vegetable oil, fish oil, animal oil or synthetically prepared oil which can be metabolized by the body of the subject to which the adjuvant will be administered and which is not toxic to the subject. The subject is an animal, preferably a member of the subphylum cordata, and more preferably a human.

The oil component of this invention may be any long-chain alkane, alkene or alkyne, or an acid, alcohol, ether or ester derivative thereof. Preferred esters include fatty-acid esters of mono- and poly-alcohols, such as mono-, di- and tri-glycerides as well as esters of 1,2-propanediol or other poly-hydroxy alcohols. Alcohols may be acylated employing a mono- or poly-functional acid, for example acetic acid, propanoic acid, citric acid or the like. Ethers derived from long chain alcohols that are oils and meet the other criteria set forth herein may also be used.

The individual long-chain alkane, alkene or alkyne moieties of the oil portion of the present invention preferably have from 6-40 carbon atoms. The moiety may have a straight or branched chain structure. It may be fully saturated or have one or more double or triple bonds.

Where the oil is a hydrocarbon, it is preferably an unsaturated branched or unbranched long-chain hydrocarbon oil (i.e., alkene or alkyne), more preferably a polyunsaturated oil having from 10-50 carbon atoms, even more preferably a branched polyunsaturated oil having from 20-40 carbon atoms.

Where mono or poly ester- or ether-based oils are employed, the 6-40 carbon preference applies to the individual fatty acid or fatty alcohol moieties, not the total carbon count. These moieties more preferably contain from 10-30 carbon atoms. Examples of fatty acids include lauric acid (12 carbons), myristic acid (14 carbons), palmitic acid (16 carbons), palmitoleic acid (16 carbons), stearic acid (18 carbons), oleic acid (18 carbons), linoleic acid (18 carbons), arachidic acid (20 carbons), arachidonic acid (20 carbons), and lignoceric acid (24 carbons).

Sources for vegetable oils include nuts, seeds and grains. Peanut oil, soybean oil, coconut oil, and olive oil, exemplify the nut oils. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used.

The technology for obtaining vegetable oils is well developed and well known. The compositions of these and other similar oils may be found in, for example, the Merck Index, and source materials on foods, nutrition and food technology.

Oils from any animal source, may be employed in the adjuvants of this invention. Animal fats are frequently solids at physiological temperatures (and hence are not "oils" as defined herein) due to the fact that they exist as triglycerides and have a higher degree of saturation than vegetable oils (or fish oils). However, oils in the form of fatty acids are obtainable from animal fats by partial or complete triglyceride saponification, which provides the free fatty acids. Oils from mammalian milk are metabolizable and may therefore be used in the practice of this invention. The procedures for separation, purification, saponification and other means necessary for obtaining pure oils from animal sources are well known in the art.

Most fish contain metabolizable oils, which may be readily recovered. For example, cod liver oil, shark liver oils, and whale oil such as spermaceti exemplify several of the fish oils that may be used herein. A number of branched chain oils are synthesized biochemically in 5-carbon isoprene units in fish and are generally referred to as terpenoids. Shark liver oil contains a branched, unsaturated, all-trans terpenoid with six isoprene units known as squalene, or 2,6,10,15,19,23-hexamethyl-2,6,10,14,18,22-tetracosahexaene, which is particularly preferred herein. Squalane, the saturated analog to squalene, is also useful. Fish oils, including squalene and squalane, are readily available from commercial sources or may be obtained by methods known in the art.

The metabolizable oil component will preferably be present in the adjuvant compositions of the present invention in an amount of from about 50 to 5000 micrograms/dose, more preferably 100 to 500 micrograms/dose.

Steroids for use in the adjuvant compositions of the present invention are derivatives of the saturated tetracyclic hydrocarbon, perhydrocyclopentanophenanthrene, and include sterols, bile acids, and hormones, such as adrenal cortical steroids, androgens, estrogens and pregestational hormones. Preferred steroids for the practice of the present invention are sterols, including cholesterol, cholesterol derivatives (e.g., dihydrocholesterol and 7-dehydrocholesterol), lanosterol, phytosterols (e.g., stigmasterol and sitosterol), and mycosterols (e.g., ergosterol). Cholesterol is most preferred.

The steroid component will preferably be present in the adjuvant compositions of the present invention in an amount of from about 10 to 1000 micrograms/dose, more preferably 50 to 100 micrograms/dose.

Saponins preferred for use in connection with the present invention are triterpenoidal saponins composed of a triterpenoid nucleus with one or more sugar-containing side chains. More preferred are saponins having a quillaic acid nucleus and one or more sugar-containing side chain, even more preferably 3,28-O-bisglycoside quillaic acid compounds. Saponins for use in connection with the present invention are typically those derived from the tree *Quillaja saponaria*. A preferred commercial product is QS21, which is available, for example, from Cambridge Bioscience, Inc. (Worcester, Mass.), which is a saponin extracted from *Quillaja saponaria* Molina tree bark. It is supplied in vials as a lyophilized powder.

The saponin component will preferably be present in the adjuvant compositions of the present invention in an amount of from about 2 to 100 micrograms/dose, more preferably 5 to 25 micrograms/dose.

As noted above, in addition to the metabolizable oil, the steroid and the saponin components, the adjuvant compositions of the present invention optionally contain at least one emulsifying agent. A substantial number of suitable emulsifying agents (also referred to as surfactants or detergents) are used in the pharmaceutical sciences, any of which are typically the useful so long as they are sufficiently non-toxic. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long chain fatty-acid-derived compounds form another substantial group of emulsifying agents that could be used in this invention.

Specific examples of suitable emulsifying agents that can be used in accordance with the present invention include the following:

1. Water-soluble soaps, such as the sodium, potassium, ammonium and alkanol-ammonium salts of higher fatty acids ($C_{10}$-$C_{22}$), and, particularly sodium and potassium tallow and coconut soaps.

2. Anionic synthetic non-soap detergents, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$-sulfonated $C_{10}$-$C_{24}$ alpha-olefins.

3. Nonionic synthetic detergents made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

4. Nonionic detergents, such as amine oxides, phosphine oxides and sulfoxides, having semipolar characteristics. Specific examples of long chain tertiary amine oxides include dimethyldodecylamine oxide and bis-(2-hydroxyethyl) dodecylamine. Specific examples of phosphine oxides are found in U.S. Pat. No. 3,304,263, which issued Feb. 14, 1967, and include dimethyldodecylphosphine oxide and dimethyl-(2hydroxydodecyl) phosphine oxide.

5. Long chain sulfoxides, including those corresponding to the formula $R_1$—SO—$R_2$ wherein $R_1$ and $R_2$ are substituted or unsubstituted alkyl radicals, the former containing from about 10 to about 28 carbon atoms, whereas $R_2$ contains from 1 to 3 carbon atoms. Specific examples of these sulfoxides include dodecyl methyl sulfoxide and 3-hydroxy tridecyl methyl sulfoxide.

6. Ampholytic synthetic detergents, such as sodium 3-dodecylaminopropionate and sodium 3-dodecylaminopropane sulfonate.

7. Zwitterionic synthetic detergents, such as 3-(N,N-dimethyl-N-hexadecylammonio)propane-1-sulfonate and 3-(N,N-dimethyl-N-hexadecylammonio)-2-hydroxy propane-1-sulfonate.

Additionally, the following types of emulsifying agents can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this and other paragraphs overlap with one another.

There are a number of emulsifying agents specifically designed for and commonly used in biological situations. For example, a number of biological detergents (surfactants) are listed as such by Sigma Chemical Company on pages 310-316 of its 1987 Catalog of Biochemical and Organic Compounds. Such surfactants are divided into four basic types: anionic, cationic, zwitterionic, and nonionic. Examples of anionic detergents include alginic acid, caprylic acid, cholic acid, 1-decanesulfonic acid, deoxycholic acid, 1-dodecanesulfonic acid, N-lauroylsarcosine, and taurocholic acid. Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate. Examples of zwitterionic detergents include 3-[(3-cholamidopropyl)-dimethylammonio]-1-propanesulfonate (commonly abbreviated CHAPS), 3-[(3-cholamidopropyl)dimethylammonio]-2-hydroxy-1-propanesulfonate (commonly abbreviated CHAPSO), N-dodecyl-N,N-dimethyl-3-ammonio-1-propanesulfonate, and lyso-alpha-phosphatidylcholine. Examples of nonionic detergents include decanoyl-N-methylglucamide, diethylene glycol monopentyl ether, n-dodecyl beta-D-glucopyranoside, ethylene oxide condensates of fatty alcohols (e.g., those sold under the trade name Lubrol), polyoxyethylene ethers of fatty acids (particularly $C_{12}$-$C_{20}$ fatty acids), polyoxyethylene sorbitan fatty acid esters (e.g., sold under the trade name Tween®), and sorbitan fatty acid esters (e.g., sold under the trade name Span®).

A particularly useful group of surfactants are the sorbitan-based non-ionic surfactants. These surfactants are prepared by dehydration of sorbitol to give 1,4-sorbitan, which is then reacted with one or more equivalents of a fatty acid. The fatty-acid-substituted moiety may be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monostearate, sorbitan monooleate, sorbitan sesquioleate, and sorbitan trioleate. These surfactants are commercially available under the name SPAN® or ARLACEL®.

SPAN® and ARLACEL® surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 and 8.6. Such surfactants can be readily made by means known in the art or are commercially available from, for example, ICI America's Inc., Wilmington, Del. under the registered mark ATLAS®.

A related group of surfactants comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN®, are useful for preparing oil-in-water emulsions and dispersions, or for the solubilization of oils and making anhydrous ointments water-soluble or washable. The TWEEN® surfactants may be combined with a related sorbitan monoester or triester surfactant to promote emulsion stability. TWEEN® surfactants generally have a HLB value falling between 9.6 and 16.7. TWEEN® surfactants are commercially available from a number of manufacturers, for example ICI America's Inc., Wilmington, Del. under the registered mark ATLAS® surfactants.

Another group of non-ionic surfactants which could be used alone or in conjunction with SPAN®, ARLACEL® and/or TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water like TWEEN® surfactants. The MYRJ® surfactants may be blended, for example, with TWEEN® surfactants or with TWEEN®/SPAN® or with ARLACEL® surfactant mixtures for use in forming emulsions. MYRJ® surfactants can be made by methods known in the art or are available commercially from ICI America's Inc.

Another group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which could potentially be used in the practice of this invention are for example: polyoxyethylenes, polyol fatty acid esters, polyoxyethylene ethers, polyoxypropylene fatty ethers, bee's wax derivatives containing polyoxyethylene, polyoxyethylene lanolin derivatives, polyoxyethylene fatty glycerides, glycerol fatty acid esters or other polyoxyethylene acid alcohols or ether derivatives of long-chain fatty acids of 12-22 carbon atoms.

Of the above emulsifying agents, the following are more preferred: sorbitan-based non-ionic surfactants such as those commercially available under the name of SPANS or ARLACEL®; polyoxyethylene sorbitan monoesters and polyoxyethylene sorbitan triesters, commercially known by the name TWEEN®; polyoxyethylene fatty acids available under the name MYRJ®; polyoxyethylene fatty acid ethers derived from lauryl, acetyl, stearyl and oleyl alcohols, such as those known by the name of BRIJ®; and the like. These substances are readily available from a number of commercial sources, including ICI America's Inc., Wilmington, Del.

In general, it is preferable to choose an emulsion-forming non-ionic surfactant that has an HLB value in the range of about 7 to 16. This value may be obtained, for example, through the use of a single non-ionic surfactant such as a TWEEN® surfactant or may be achieved by the use of a blend of a sorbitan fatty acid ester in combination with a polyoxyethylene sorbitan fatty acid ester; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

The optional emulsifying agent(s) will preferably be present in the adjuvant compositions of the present invention in an amount of from about 0.1 to 100 micrograms/dose, more preferably 2 to 10 micrograms/dose.

Other optional species for use with the adjuvant compositions of the present invention are muramyl peptides, such as muramyl dipeptides and muramyl dipeptide derivatives such as MTP-PE. As noted above, MTP-PE is a muramyl tripeptide that includes phospholipid tails to allow association of the hydrophobic portion of the molecule with a lipid environment while the muramyl peptide portion associates with the aqueous environment. For example, MTP-PE may be present in an amount of about 0-500 micrograms/dose, more preferably 0-250 micrograms/dose and most preferably, 0-100 micrograms/dose.

If desired, further adjuvants known in the art can be added to the adjuvant compositions of the present invention.

The adjuvant compositions of the present invention are prepared using any of several methods well known in the art. Preferably, the adjuvant compositions of the present invention are in the form of oil-in-water emulsions with submicron particles, i.e., emulsion with dispersed (oil) phase particles less than about 1 micron in diameter and in the nanometer size range. In order to produce such emulsions, a number of techniques can be used. For example, commercial emulsifiers can be used, which operate by the principle of high shear forces developed by forcing fluids through small apertures under high pressure. Examples of commercial emulsifiers include, without limitation, Model 110Y microfluidizer (Microfluidics, Newton, Mass.), Gaulin Model 30CD (Gaulin, Inc., Everett, Mass.), and Rainnie Minilab Type 8.30H (Miro Atomizer Food and Dairy, Inc., Hudson, Wis.). The appropriate pressure for use with an individual emulsifier is readily determined by one of skill in the art.

The size of the oil droplets can be varied, for instance, by changing the components within the adjuvant composition and their relative amounts. For instance: (a) increasing the ratio of emulsifying agents (including the saponin, the optional emulsifying agents(s)) to oil (including the metabolizable oil and the sterol) decreases particle size, (b) increasing operating pressure reduces particle size, and (c) increasing temperature decreases particle size. Droplet size can be verified by use of sizing instruments, such as the commercial Sub-Micron Particle Analyzer (Model N4MD) manufactured by the Coulter Corporation, and the parameters can be varied using the guidelines including those set forth above until substantially all droplets are preferably less than 1 micron in diameter, more preferably less than about 0.8 microns in diameter, and most preferably less than about 0.5 microns in diameter. By "substantially all" is meant at least about 80% (by number), preferably at least about 90%, more preferably at least about 95%, and most preferably at least about 98%. The particle size distribution is typically Gaussian, so that the average diameter is substantially smaller than the stated limits.

According to one embodiment of the present invention, an organic solvent appropriate for the dissolution of the cholesterol and metabolizable oil components of the composition is selected, and the cholesterol and metabolizable oil components are dissolved therein to provide a solvent-based phase. At the same time, the saponin component of the adjuvant composition is dispersed or dissolved in water or other aqueous solution to provide a water-based phase. The optional components, such as the emulsifying agent(s) or the muramyl peptide compound can be dissolved or dispersed in either phase, preferably the phase which is most compatible for the optional component of interest. As a specific example, as seen from Example 1 below, cholesterol, squalene and SPAN 85® sorbitan fatty acid ester can be dissolved/dispersed in chloroform to form the solvent-based phase, while QS21 saponin extract and TWEEN 80® polyoxyethylene sorbitan fatty acid ester can be dissolved/dispersed in water to form the water-based phase (where provided, the muramyl peptide can be dissolved/dispersed in the oil phase). After formation of the solvent- and water-based phases, they are combined and preferably subjected to a high-shear apparatus to create an emulsion containing dispersed (oil) phase particles of the desired size. The process is preferably completed by the removal of any residual organic solvent.

The compositions will typically comprise a therapeutically effective amount of an antigen of interest. The exact amount necessary will vary, depending on the subject being treated; the age and general condition of the subject to be treated; the capacity of the subject to mount an appropriate immune response; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. For example, for purposes of the present invention, where the antigen is a polynucleotide, an effective dose will typically range from about 1 ng to about 1 mg, more preferably from about 10 ng to about 1 μg, and most preferably about 50 ng to about 500 ng of the antigen delivered per dose; where the antigen is a polypeptide, an effective dose will typically range from about 1 μg to about 100 mg, more preferably from about 10 μg to about 1 mg, and most preferably about 50 μg to about 500 μg of the polypeptide per dose.

The antigen of interest can be provided within the adjuvant/antigen compositions of the present invention by a number of techniques. The adjuvant compositions are generally prepared from the components described above prior to adding the antigen that will be used in the vaccine. As previously noted, it may be desirable to initially prepare the adjuvant composition using, for example, unadulterated water (e.g., deionized water), following by the addition of the antigen within a buffer solution, to provide the final composition with an appropriate osmolality and pH.

Since the adjuvant compositions of the invention are typically stable, the antigen and emulsion can mixed by simple shaking. Other techniques, such as passing a mixture of the adjuvant and solution or suspension of the antigen rapidly through a small opening (such as a hypodermic needle), readily provide a useful vaccine composition. However, it is not essential that the antigen of interest be added after formation of the adjuvant composition. Instead, the antigen can be added, for example, to the appropriate phase (typically the water-based phase) prior to emulsification during the adjuvant formation process.

Depending upon the final dosage form that is produced, the antigen/adjuvant compositions of the invention can include additional excipients such as those listed above, as is known in the art.

Once formulated, the compositions of the invention are preferably administered parenterally, e.g., by injection. The compositions can be injected either subcutaneously, intraperitoneally, intravenously or intramuscularly. However, other modes of administration are possible, including nasal, mucosal, rectal, vaginal, oral and pulmonary administration, suppositories, and transdermal or transcutaneous applications.

Treatment may be a single dose schedule or a multiple dose schedule. A multiple dose schedule is one in which a primary course of administration may be with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also, at least in part, be determined by the need of the subject and be dependent on the judgment of the practitioner.

If prophylactic treatment of disease is desired, the antigens in vaccines are generally administered prior to primary infection with the pathogen of interest. If therapeutic treatment is desired, e.g., the reduction of symptoms or recurrences, the antigens are generally administered subsequent to primary infection.

C. Experimental

Below are examples for carrying out specific embodiments of the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

A solvent-based phase is created by first dissolving 840 ul of 20 mg/ml cholesterol, available from Avanti Lipids, Inc., in chloroform, placing it in a 100 ml beaker and leaving it in a laboratory hood until the volume is reduced to approximately 400 ul. 200 ul of Span® 85, a sorbitan fatty acid ester available from Sigma Chemicals, and 2 ml squalene, a terpenoid commonly obtained from shark liver oil and available from Sigma Chemicals, are then added, followed by mixing.

A water-based phase is created by first adding 200 ul Tween® 80, a polyoxyethylene sorbitan fatty acid ester available from Sigma Chemicals, to 37.6 ml D.I. water, and mixing by stirring for 15 minutes. 1 ml of 4 mg/ml QS21 in water, a saponin extract available from Aquilla Inc., is then added and mixed with the Tween® solution.

The water-based phase is added to the solvent-based phase and the mixture homogenized with a 10 mm probe of the Omni benchtop homogenizer (LabTek Inc, US) for 1 minute. The resulting emulsified mixture is passed five times through a microfluidizer (M110, Microfluidics, USA) at 90 psi.

The residual chloroform is allowed to evaporate for 10-20 minutes. The resulting emulsion contains the following components in the following amounts: (a) 42 mg/ml squalene, (b) 4.8 mg/ml Span® 85, (c) 5 mg/ml Tween® 80, (d) 425 ug/ml cholesterol, and (e) 100 ug/ml QS21.

EXAMPLE 2

10 ul of 1 mg/ml HIV p24 gag (Protein Purification Group, Chiron Corp.) in PBS is mixed with 40 ul PBS. This mixture is then added to 50 ul of the emulsion produced in Example 1, followed by gentle mixing and injection into Balb/C mice. The animals are immunized twice at 4 weeks interval and then bled at day 42. The sera are then assayed by established HIV p24 ELISA to determine total Ig and Ig2a titers against HIV p24. Results corresponding to this MF59(chol)/QS21 formulation are presented in FIG. 1.

For comparison, the formulations to follow are made and injected into Balb/C mice as above. Results are presented in FIG. 1.

MF59 formulation (comparative): The MF59 emulsion is formed by combining 5% w/v of Squalene (Sigma) and 0.05% w/v of Span® 85 (the oil phase) with 0.05% w/v of Tween® 80 in D.I. water (100 ml). The mixture is homogenized with a 10 mm probe of the Omni benchtop homogenizer for 1 minute. The resulting emulsified mixture is passed five times through an M110 microfluidizer at 90 psi.

MF59/QS21 formulation (comparative): A formulation like that the MF59 formulation above (100 ml), except that 1.25 ml of 4 mg/ml QS21 in water is added and mixed with the Tween® water-based phase prior to emulsification and passage through the microfluidizer.

MF59/CpG1 formulation (comparative): A formulation like that the MF59 formulation above, except that 10 ul CpG (1 mg/ml) (Oligos Inc., USA) are added to the formulation just prior to immunization.

EXAMPLE 3

MF59(chol)/QS21, MF59 (comparative) and MF59/CpG1 (comparative) formulations are made as above, except that the 10 ul of 1 mg/ml HIV p24 gag in PBS is replaced with 2 ul of 1 mg/ml HCV E2 viral protein (Protein Purification Group, Chiron Corp.) in PBS. The formulations are injected into Balb/C mice as above, and the sera were assayed by established HCV E2 ELISA to determine total Ig, Ig1 and Ig2a titers against HCV E2. Results are presented in FIG. 2.

Figure 2:
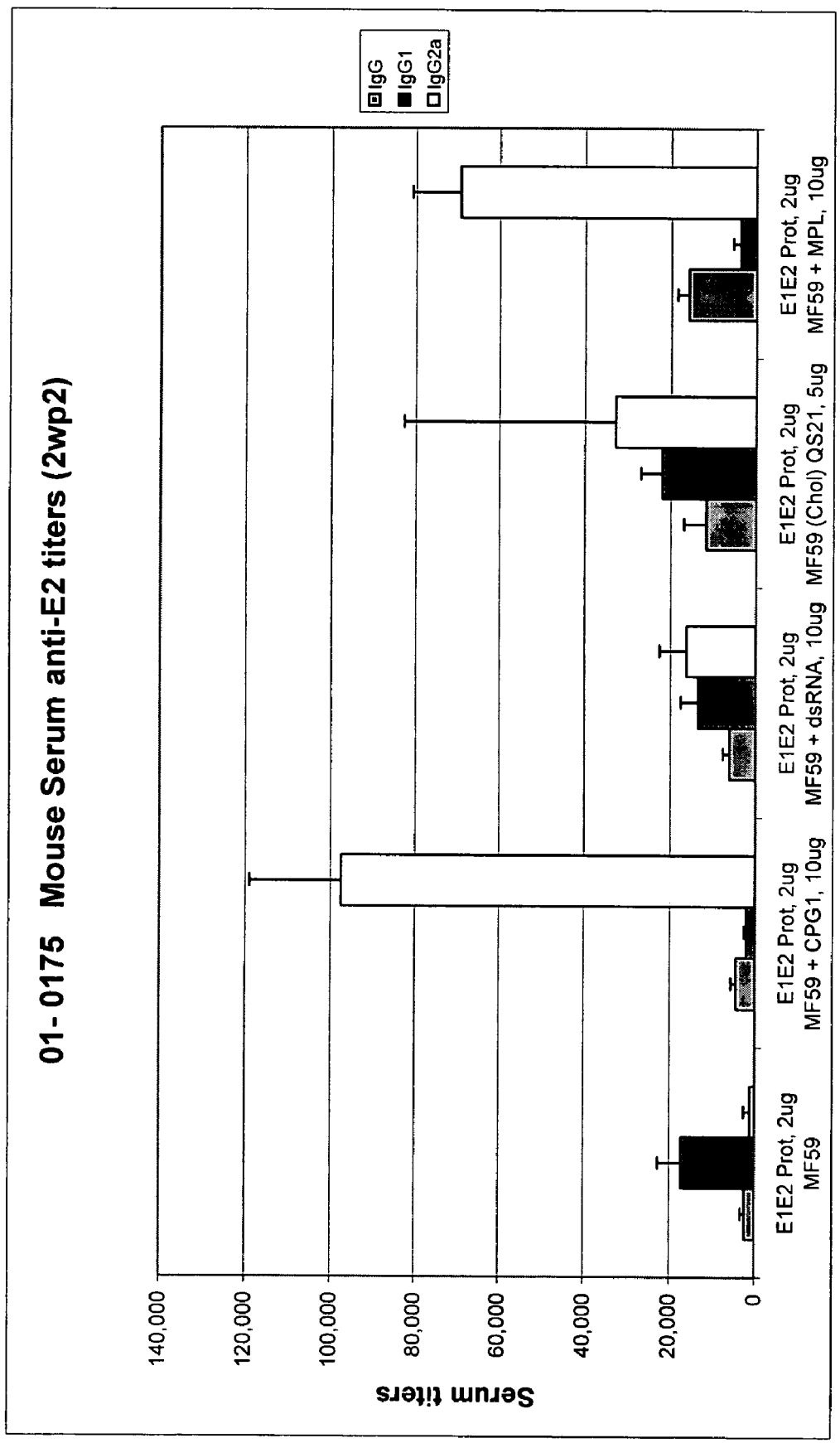
FIG. 2 is a bar graph illustrating IgG, IgG1 and IgG2a serum titers for five injectable formulations.

Additional comparative formulations presented in FIG. 2 are as follows:

MF59/dsRNA formulation (comparative): A formulation like that the MF59 formulation, except that 10 ul dsRNA (1 mg/ml) (Sigma Chemicals) are added to the formulation just prior to immunization.

MF59/MPL formulation (comparative): A formulation like the MF59 formulation, except that monophosphorylipid A (MPL) (5.0 ml ) in chloroform (1 mg/ml) is added to the squalene oil phase prior to emulsification and passage through the microfluidizer.

Although preferred embodiments of the subject invention have been described in some detail, it is understood that obvious variations can be made without departing from the spirit and the scope of the invention, as defined by the appended claims.

REFERENCES

Ref. 1—International patent application WO99/24578.
Ref. 2—International patent application WO99/36544.
Ref. 3—International patent application WO99/57280.
Ref. 4—International patent application WO00/22430.
Ref. 5—Tettelin et al., (2000) *Science* 287:1809-1815.
Ref. 6—International patent application WO96/29412.
Ref. 7—Pizza et al. (2000) *Science* 287:1816-1820.

Ref. 8—International patent application PCT/IB01/00166.
Ref. 9—Bjune et al. (1991) *Lancet* 338(8775):1093-1096.
Ref. 10—Fukasawa et al. (1990) *Vaccine* 17:2951-2958.
Ref. 11—Rosenqvist et al. (1998) *Dev. Biol. Stand.* 92:323-333.
Ref. 12—Costantino et al. (1992) *Vaccine* 10:691-698.
Ref. 13—Costantino et al. (1999) *Vaccine* 17:1251-1263.
Ref. 14—Watson (2000) *Padiatr Infect Dis J* 19:331-332.
Ref. 15—Rubin (2000) *Pediatr Clin North Am* 47:269-285, v.
Ref. 16—Jedrzejas (2001) *Microbiol Mol Biol Rev* 65:187-207.
Ref. 17—International patent application filed on 3rd Jul. 2001 claiming priority from GB-0016363.4.
Ref. 18—Kalman et al. (1999) *Nature Genetics* 21:385-389.
Ref. 19—Read et al. (2000) *Nucleic Acids Res* 28:1397-406.
Ref. 20—Shirai et al. (2000) *J. Infect. Dis.* 181(Suppl 3):S524-S527.
Ref. 21—International patent application WO99/27105.
Ref. 22—International patent application WO00/27994.
Ref. 23—International patent application WO00/37494.
Ref. 24—International patent application WO99/28475.
Ref. 25—Bell (2000) *Pediatr Infect Dis J* 19:1187-1188.
Ref. 26—Iwarson (1995) *APMIS* 103:321-326.
Ref. 27—Gerlich et al. (1990) *Vaccine* 8 Suppl:S63-68 & 79-80.
Ref. 28—Hsu et al. (1999) *Clin Liver Dis* 3:901-915.
Ref. 29—Gustafsson et al. (1996) *N. Engl. J. Med.* 334:349-355.
Ref. 30—Rappuoli et al. (1991) *TIBTECH* 9:232-238.
Ref. 31—*Vaccines* (1988) eds. Plotkin & Mortimer. ISBN 0-7216-1946-0.
Ref. 32—Del Guidice et al. (1 998) *Molecular Aspects of Medicine* 19:1-70.
Ref. 33—International patent application WO93/18150.
Ref. 34—International patent application WO99/533 10.
Ref. 35—International patent application WO98/04702.
Ref. 36—Ross et al. (2001) *Vaccine* 19:4135-4142.
Ref. 37—Sutter et al. (2000) *Pediatr Clin North Am* 47:287-308.
Ref. 38—Zimmerman & Spann (1999) *Am Fam Physician* 59:113-118, 125-126.
Ref. 39—Dreesen (1997) *Vaccine* 15 Suppl:S2-6.
Ref. 40—*MMWR Morb Mortal Wkly Rep* 1998 Jan. 16;47(1):12, 19.
Ref. 41—McMichael (2000) *Vaccine* 19 Suppl 1:S101-107.
Ref. 42—Schuchat (1999) *Lancet* 353(9146):51-6.
Ref. 43—GB patent applications 0026333.5, 0028727.6 & 0105640.7.
Ref. 44—Dale (1999) *Infect Dis Clin North Am* 13:227-43, viii.
Ref. 45—Ferretti et al. (2001) *PNAS USA* 98:4658-4663.
Ref. 46—Kuroda et al. (2001) *Lancet* 357(9264):1225-1240; see also pages 1218-1219.
Ref. 47—Ramsay et al. (2001) *Lancet* 357(9251):195-196.
Ref. 48—Lindberg (1999) *Vaccine* 17 Suppl 2:S28-36.
Ref. 49—Buttery & Moxon (2000) *J R Coll Physicians London* 34:163-168.
Ref. 50—Ahmad & Chapnick (1999) *Infect Dis Clin North Am* 13:113-133, vii.
Ref. 51—Goldblatt (1998) *J. Med. Microbiol.* 47:563-567.
Ref. 52—European patent 0 477 508.
Ref. 53—U.S. Pat. No. 5,306,492.
Ref. 54—International patent application WO98/42721.
Ref. 55—*Conjugate Vaccines* (eds. Cruse et al.) ISBN 3805549326, particularly vol. 10:48-114.
Ref. 56—Hermanson (1996) *Bioconjugate Techniques* ISBN: 0123423368 & 012342335X.
Ref. 57—European patent application 0372501.
Ref. 58—European patent application 0378881.
Ref. 59—European patent application 0427347.
Ref. 60—International patent application WO93/17712.
Ref. 61—International patent application WO98/58668.
Ref. 62—European patent application 0471177.
Ref. 63—International patent application WO00/56360.
Ref. 64—International patent application WO00/61761.

The invention claimed is:

1. An oil-in-water adjuvant composition comprising water, a metabolizable oil comprising at least one branched or unbranched long-chain hydrocarbon moiety, a steroid, a saponin and a muramyl tripeptide, wherein said adjuvant composition is formed by a method comprising: (a) emulsifying a mixture comprising (i) water, (ii) a water-immiscible organic solvent, (iii) said metabolizable oil, (iv) said steroid, (v) said saponin and (vi) said muramyl tripeptide; and (b) removing the organic solvent from the emulsion that is formed in step (a), such that an oil-in-water emulsion is formed in which at least 80% by number of the oil droplets within the emulsion are less than 1 micron in diameter.

2. The oil-in-water adjuvant composition of claim 1, further comprising at least one emulsifying agent.

3. The oil-in-water adjuvant composition of claim 2, wherein said at least one emulsifying agent comprises at least one non-ionic surfactant.

4. The oil-in-water adjuvant composition of claim 3, wherein said at least one non-ionic surfactant comprises a fatty acid ester.

5. The oil-in-water adjuvant composition of claim 4, wherein said fatty acid ester comprises a polyoxyethylene moiety.

6. The oil-in-water adjuvant composition of claim 3, wherein said at least one non-ionic surfactant comprises at least one sorbitan derivative.

7. The oil-in-water adjuvant composition of claim 6, wherein said at least one sorbitan derivative is selected sorbitan fatty acid monoesters, sorbitan fatty acid sesquiesters, sorbitan fatty acid triesters, polyoxyethylene sorbitan fatty acid monoesters and polyoxyethylene sorbitan fatty acid triesters.

8. The oil-in-water adjuvant composition of claim 6, wherein said at least one sorbitan derivative comprises polyoxyethylene sorbitan monooleate and sorbitan trioleate.

9. The oil-in-water adjuvant composition of claim 1 or 2, wherein said steroid is a sterol.

10. The oil-in-water adjuvant composition of claim 9, wherein said sterol is cholesterol.

11. The oil-in-water adjuvant composition of claim 9, wherein said saponin is a triterpenoidal saponin.

12. The oil-in-water adjuvant composition of claim 9, wherein said saponin is a 3,28-O-bisglycoside quillaic acid compound.

13. The oil-in-water adjuvant composition of claim 9, wherein said saponin is a saponin extracted from *Quillaja saponaria*.

14. The oil-in-water adjuvant composition of claim 9, further comprising an antigen.

15. The oil-in-water adjuvant composition of claim 14, wherein the antigen is a polypeptide or a polynucleotide.

16. The oil-in-water adjuvant composition of claim 14, wherein the antigen is a polypeptide selected from HIV polypeptide antigens, meningitis B polypeptide antigens, streptococcus B polypeptide antigens, hepatitis C polypeptide antigens, *Helicobacter pylori* polypeptide antigens, and Influenza A hemagglutinin polypeptide antigens.

17. The oil-in-water adjuvant composition of claim 14, wherein the antigen is a polynucleotide which encodes a polypeptide antigen selected from the group consisting of an HIV polypeptide antigen, a meningitis B polypeptide antigen, a streptococcus B polypeptide antigen, a hepatitis C polypeptide antigen, a *Helicobacter pylori* polypeptide antigen and an Influenza A hemagglutinin polypeptide antigen.

18. The oil-in-water adjuvant composition of claim 14, further comprising a pharmaceutically acceptable excipient.

19. A method of treating a disease comprising:
   a. providing the oil-in-water adjuvant composition of claim 14; and
   b. administering said adjuvant composition to a vertebrate subject.

20. A method of vaccination comprising:.
   a. providing the oil-in-water adjuvant composition of claim 14; and
   b. administering said adjuvant composition to a vertebrate subject.

21. A method of raising an immune response comprising:
   a. providing the oil-in-water adjuvant composition of claim 14; and
   b. administering said adjuvant composition to a vertebrate subject.

22. A method of delivering a therapeutically effective amount of an antigen to a vertebrate subject, said method comprising:
   a. providing the oil-in-water adjuvant composition of claim 14; and
   b. administering said adjuvant composition to a vertebrate subject.

23. A method of producing an oil-in-water adjuvant composition, said method comprising:
   (a) forming the oil-in-water adjuvant composition of claim 1; and
   (b) adding an antigen to said oil-in-water emulsion.

24. The method of claim 23, wherein said emulsion further comprises at least one emulsifying agent.

25. The method of claim 23 or 24, wherein the antigen is a polypeptide or a polynucleotide.

26. The method of claim 25, wherein the antigen is a polypeptide selected from HIV polypeptide antigens, meningitis B polypeptide antigens, streptococcus B polypeptide antigens, hepatitis C polypeptide antigens, *Helicobacter pylori* polypeptide antigens, and Influenza A hemagglutinin polypeptide antigens.

27. The method of claim 25, wherein the antigen is a polynucleotide which encodes a polypeptide antigen selected from the group consisting of an HIV polypeptide antigen, a meningitis B polypeptide antigen, a streptococcus B polypeptide antigen, a hepatitis C polypeptide antigen, a *Helicobacter pylori* polypeptide antigen and an Influenza A hemagglutinin polypeptide antigen.

28. The oil-in-water adjuvant composition of claim 1, wherein said metabolizable oil comprises squalene.

29. The oil-in-water adjuvant composition of claim 1, wherein said muramyl tripeptide is N-acetylmuramyl-L-alanyl-D-isogluatminyl-L-alanine-2-(1'-2'-dipalmitoyl-sn-glycero-3-huydroxyphosphoryloxy)-ethylamine (MTP-PE).

* * * * *